United States Patent [19]

Gray et al.

[11] Patent Number: 5,602,890
[45] Date of Patent: Feb. 11, 1997

[54] CONTAINER FILL LEVEL AND PRESSURIZATION INSPECTION USING MULTI-DIMENSIONAL IMAGES

[75] Inventors: Glenn Gray, Waipshu, Hi.; Clayton Wood, Framingham; Helmut W. Klotzsch, Groton, both of Mass.

[73] Assignee: Thermedics Detection Inc., Chelmsford, Mass.

[21] Appl. No.: 534,846

[22] Filed: Sep. 27, 1995

[51] Int. Cl.⁶ ............................................. G01N 23/10
[52] U.S. Cl. ............................. 378/57; 378/56; 378/58
[58] Field of Search .................... 378/57, 52, 51, 378/58, 62, 98.12

[56] References Cited

U.S. PATENT DOCUMENTS

| | | | |
|---|---|---|---|
| 2,999,591 | 9/1961 | Crump | 209/82 |
| 3,007,048 | 10/1961 | Knapp et al. | 250/43.5 |
| 3,038,606 | 6/1962 | Leaver et al. | 209/111.5 |
| 3,133,638 | 5/1964 | Calhoun | 209/82 |
| 3,218,463 | 11/1965 | Calhoun | 250/222 |
| 3,454,759 | 7/1969 | Calhoun | 250/43.5 |
| 3,784,827 | 1/1974 | Calhoun | 250/106 S |
| 3,818,232 | 6/1974 | Kirkpatrick | 378/52 |
| 3,958,078 | 5/1976 | Fowler et al. | 178/6.8 |
| 4,055,252 | 10/1977 | Klamm et al. | 209/74 M |
| 4,182,451 | 1/1980 | Watson | 209/524 |
| 4,390,782 | 6/1983 | Vornfett | 250/223 B |
| 4,392,237 | 7/1983 | Houston | 378/51 |
| 4,415,980 | 11/1983 | Buchanan | 378/58 |
| 4,481,595 | 11/1984 | Schiessl et al. | 364/562 |
| 4,722,096 | 1/1988 | Dietrich et al. | 378/57 |
| 4,756,015 | 7/1988 | Doenges et al. | 378/57 |
| 4,788,704 | 11/1988 | Donges et al. | 378/99 |
| 4,791,655 | 12/1988 | Nagata et al. | 378/57 |
| 4,879,734 | 11/1989 | Schreckendgust et al. | 378/57 |
| 5,056,124 | 10/1991 | Kakimoto et al. | 378/57 |
| 5,097,494 | 3/1992 | Pantelleria et al. | 378/110 |
| 5,202,932 | 4/1993 | Cambier et al. | 382/8 |

OTHER PUBLICATIONS

Centro Kontrollsysteme GmbH, product brochure, Jul. 26, 1994.
Food Instrument Corporation, "ADR–50C," product brochure. No date.
Food Instrument Corporation, "ADR 50–CRM," product brochure. No date.
Heuft Systemtechnik GmbH, "Empty Bottle Inspection," product brochure. No date.
Industrial Dynamics Company, Ltd., "FT–50 Fill Level Inspection System," Form 2456, product brochure, Jul. 1992.
Industrial Dynamics Company, Ltd., "Filtec FT–50 Inspection System, Machine Specifications," Form #2552, Feb. 26, 1993.
Industrial Dynamics Company, Ltd., "Filtec Filler Monitor and Sampling System for Bottles Sales Information Manual and Machine Specifications," Form 2579, Sep. 1993.

(List continued on next page.)

*Primary Examiner*—David P. Porta
*Attorney, Agent, or Firm*—Fish & Richardson P.C.

[57] ABSTRACT

A container inspection system for inspecting a moving container includes a radiation source positioned to direct radiation at the moving container. A radiation detector is positioned to receive a portion of the radiation from the radiation source that is not absorbed or blocked by the moving container and to generate electrical signals in response thereto. Processing circuitry produces multi-dimensional image data for the moving container based on the electrical signals generated by the radiation detector, and compares at least a first portion of the multi-dimensional image data to a corresponding portion of the multi-dimensional image data for a standard container. Thereafter, the processing circuitry determines, based on a result of the comparison, one or more characteristics of the container from the set of characteristics including the fill level of the container, whether the container is underfilled, whether the container is overfilled, whether the container is properly pressurized, and whether the container is sealed.

65 Claims, 13 Drawing Sheets

OTHER PUBLICATIONS

Peco Controls Corporation, "Gamma 101P Fill Level Monitor," product brochure. No date.

Stratec Control Systems, "HF–Fill–Level–Inspection," product brochure. No date.

Stratec Control Systems, "X–Ray Fill–Level Inspection," product brochure. No date.

Stratec Control Systems, "Optical Fill–Level–Inspection," product brochure. No date.

TapTone Container Inspection Systems, "TapTone II Pressure/Vacuum Analyzer," product brochure, Feb. 1994.

TapTone Container Inspection Systems, "Automatic Full Swelled Can Detector (SCD) Popped Button Detector (PBD), Model 4104–4," product brochure. No date.

TapTone Container Inspection Systems, "Tracker Pressure/Vacuum Monitor," product brochure, Mar. 1990.

TapTone Container Inspection Systems, "TapTone Container Inspection Systems," product brochure. No date.

TapTone Container Inspection Systems, "Portable Vacuum/Pressure Tester, Model 4049," product brochure, 1988.

5,602,890

CONTAINER FILL LEVEL AND PRESSURIZATION INSPECTION USING MULTI-DIMENSIONAL IMAGES

BACKGROUND OF THE INVENTION

In container filling processes such as canning or bottling lines, it is often useful to monitor characteristics of the containers being filled. For example, the levels to which containers have been filled may be monitored for quality control purposes.

It is known to use a radiation source and a detector to determine the fill level of a container. For example, Schiessl et al., U.S. Pat. No. 4,481,595, describes a system that passes containers through a gamma radiation beam projected from a beam source to a detector. As a container passes through the beam, the system counts radiation pulses received by the detector. Once the entire container has passed through the beam, the system determines the average rate at which radiation pulses were received by the detector and compares this rate to a reference rate. Based on this comparison, the system produces a signal indicative of whether material in the container is at a high enough level to attenuate the beam. The system can be configured to detect underfill conditions by orienting the source and detector so that detected pulses pass through the container at a level below the expected fill level. Similarly, the system can be configured to detect overfill conditions by orienting the source and detector so that detected pulses pass through the container at a level above the expected fill level.

SUMMARY OF THE INVENTION

The invention includes a container inspection system that produces a multi-dimensional image of each container to be inspected. The system then analyzes the image to provide real time monitoring of characteristics such as the product fill level, the presence and proper placement of lids, the container pressure, headspace foam density, and leakage for containers moving at typical process rates on a conveyor of a container filling process. As used herein, the term "container" refers to cans, bottles and other packages whose intended contents are generally known.

The system provides accurate measurements at conveyor speeds on the order of 2400 containers per minute, and is capable of inspecting containers made from a wide variety of materials, including metal, plastic, glass and foil. If the system determines that a container is improperly filled, improperly pressurized or otherwise defective, the system automatically initiates appropriate action such as rejection of the container from the filler line and/or adjustment of filler operation. The system maintains a complete record of all rejections and their causes; a system operator may use this diagnostic data in maintaining or improving process efficiency.

The system provides significant advantages over prior art systems that provided only "go/no go" or gross "underfill/overfill" indications. For example, the system uses the multi-dimensional information about the containers to provide fill-level measurements having an accuracy to within 0.5 mm over a range of inspection speeds. This high level of accuracy permits tighter fill level thresholds and thereby reduces the number of false rejections, which in turn improves the efficiency of the inspection process.

The system uses a radiation source such as a low power x-ray source with a multi-element, linear detector to inspect filled containers moving on a conveyor line. As a container moves on the conveyor line, it passes between the radiation source and the detector array so that radiation produced by the radiation source passes through the container before being detected by the detector array.

Due to differences in path length and radiation absorption coefficients, radiation is absorbed differently by the container, the lid of the container, the contents of the container, and any air or other material above the contents of the container. These differences in absorption are measured as changes in intensity of radiation received by the detector array.

When the conveyor is oriented to move the containers in a horizontal direction, the radiation source and the detector array are positioned to define a vertical plane between the source and the detector, and are oriented so that the plane is perpendicular to the direction of motion of the conveyor. Accordingly, at any particular time, the radiation received by the detector array corresponds to a vertical slice of a container. By repeatedly receiving and storing data from the detector array as the conveyor moves the container, the system produces a multi-dimensional image of the container, where the resolution of the image is controlled by the number of elements in the detector array and the frequency at which data is received and stored. Thereafter, the system processes the image data to monitor characteristics such as fill level and pressurization and detect conditions such as underfill, overfill, low pressure, high pressure, missing or damaged lids, and bulging containers. In determining the fill level, the system may account for the presence of foam by determining foam density and the level (amount) of liquid attributable to the foam and adding the amount to the apparent fill level (amount). The system may also monitor conditions such as container wall thickness.

The system provides several advantages over the prior art. In particular, the system monitors for overfill, underfill, actual fill level, low pressure containers, missing lids, bulging containers, container wall thickness, and foam characteristics. Significantly, the system performs all of these operations simultaneously using a single sensor. The system accurately determines the fill level and other characteristics even in inspection areas in which there is significant agitation of the contents of the containers (i.e., system performance is unaffected by movement of container contents). The system compensates for such movement by collecting information about the presence of liquid in a relatively large area of the container and combining the information to determine the fill level. This permits the system to be positioned, for example, on or immediately after a curve of the conveyor or immediately after containers have been flipped over.

The system monitors for low pressure (leaking) containers without manipulating the containers. By contrast, in the prior art, leaking containers were detected by inverting the containers, allowing liquid to drain out, and thereafter detecting a low pressure container using an underfill detector. This required means for inverting the containers and further required the leak to be large enough to permit sufficient liquid to drain out of the container during the inspection process.

The system is easily calibrated by passing a standard gauge or container through the system and producing a standard image that includes all pertinent information about the desired characteristics of the containers to be inspected. The system automatically adjusts for container height and therefore may accommodate changes in container size during production with no recalibration. For example, the system may include a motorized stand that automatically positions the unit at a preset inspection point.

The system also is relatively insensitive to variations in container position due to conveyor wear or other factors. Conveyor wear, for example, may cause one or more containers to be positioned lower than other containers. When the system detects such an imperfectly positioned container, the system automatically adjusts the inspection zone to account for the change in container position.

To reject unacceptable containers, the system employs an intelligent rejector system. Sensors monitor rejector performance to verify proper rejection and collect information about wear and other factors. This information is used to compensate for the effects of wear and permit early diagnosis and correction of problems. A dual rejector may be employed to reject two successive containers and to provide redundancy if one rejector fails.

The system's ability to accurately measure fill level may also be employed to monitor and adjust filler operation. By constantly adjusting the filler valves, the system optimizes filler performance and minimizes waste.

Other features and advantages of the invention will become apparent from the following description of the preferred embodiments, and from the claims.

DESCRIPTION OF THE PREFERRED EMBODIMENTS

Figure 1:
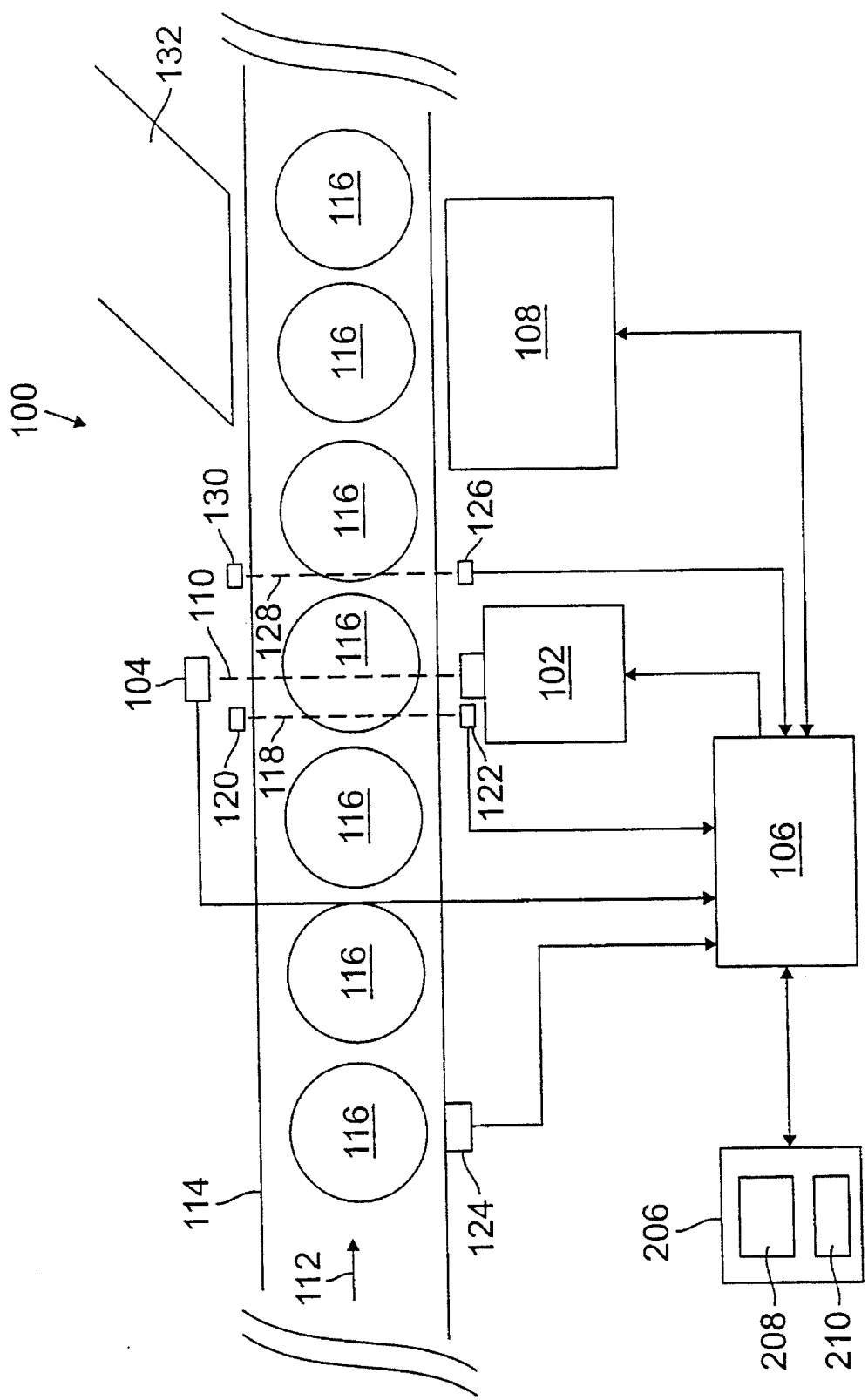
FIG. 1 is a block diagram of a container inspection system.
Figure 2:
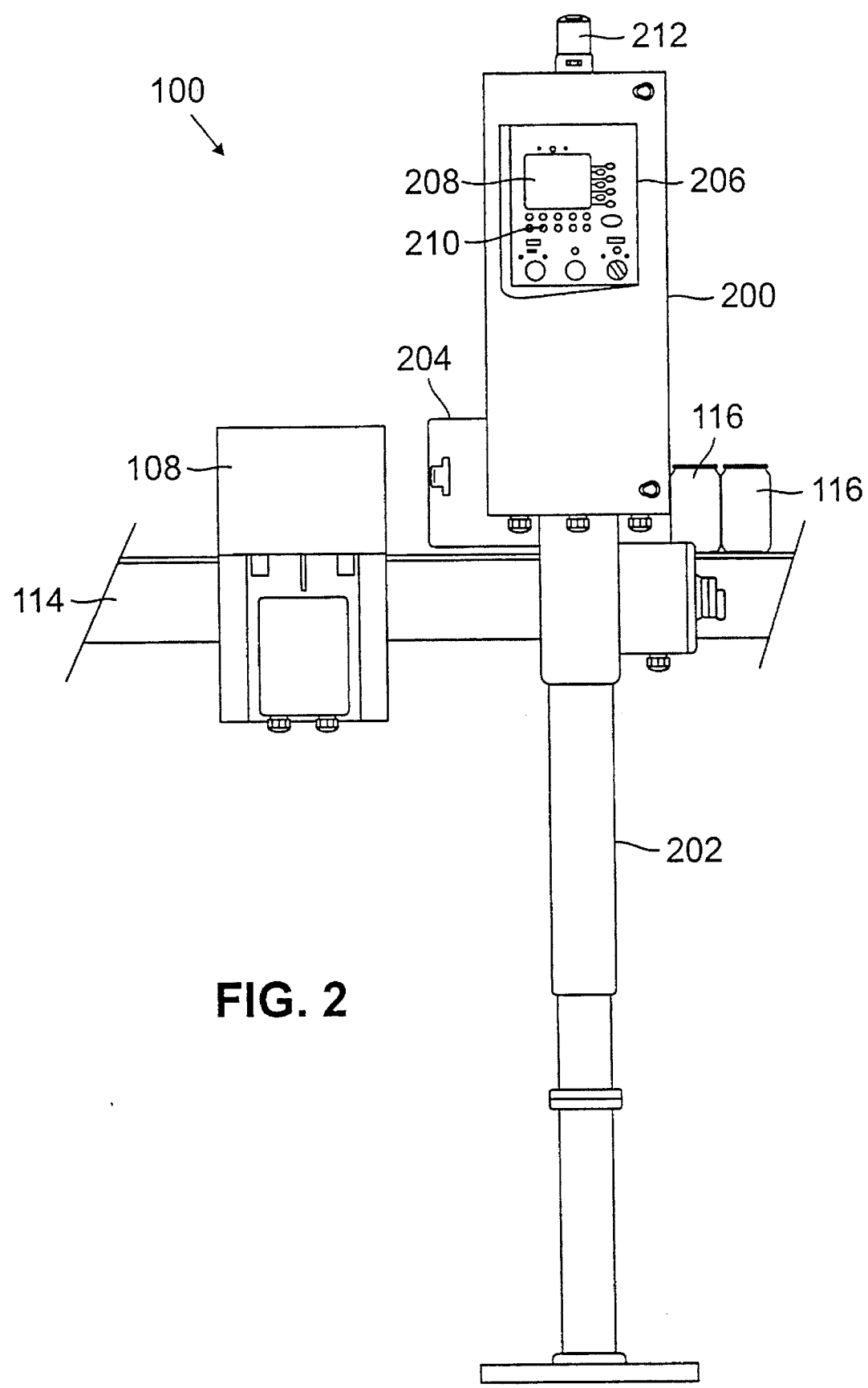
FIG. 2 is a front view of an embodiment of the container inspection system of FIG. 1.

With reference to FIG. 1, a container inspection system 100 includes an x-ray source 102, a multi-element, linear, diode detector array 104, a controller 106 and a rejector 108. The x-ray source 102 is configured to produce a vertically planar x-ray beam 110 that is received by the detector array 104. The beam 110 is perpendicular to a direction of motion 112 of a conveyor 114. The detector array 104 includes 32 diode elements, each of which provides to the controller 106 an analog signal corresponding to the x-ray radiation incident on the diode.

As a container 116 (e.g., a beverage can) approaches the x-ray beam 110, the container interrupts a light beam 118 between a light source 120 and an optical container trigger 122, which causes the container trigger 122 to send a signal to the controller 106. The controller 106 responds by periodically storing the analog signals received from the detector array 104. At any given time, a scan of the signals produced by the detector array 104 corresponds to a one dimensional (vertical) x-ray image of the container 116 as it passes in front of the array. Successive scans are made as the motion of the conveyor 114 causes the container 116 to traverse the face of the detector array 104 in the horizontal direction.

The controller 106 synchronizes successive scans of the detector array with the motion of the container 116 by simultaneously monitoring the output of an encoder 124 that is mechanically linked to the conveyor 124. The encoder 124 produces a series of pulses that each correspond to a portion of a rotation of a drive shaft of the conveyor 114. The controller 106 counts these pulses to monitor the position of the containers 116. This allows the controller 106 to control the horizontal scan rate based on the container's instantaneous speed so that each vertical scan is initiated at a fixed horizontal distance (independent of speed) with respect to the container's leading edge. In this manner, the controller 106 stores in memory an accurate two dimensional image of the x-ray absorption characteristics of the container 116 as the container 116 passes in front of the detector array 104.

Once the container 116 has passed. completely through the x-ray beam 110, the controller 106 processes the image data to determine whether the container 116 is improperly filled or otherwise defective. If so, the controller 106 activates the rejector 108, and the rejector 108 removes the defective container 116 from the conveyor 114.

In addition to the container trigger 122, the system includes a rejector trigger 126 that produces a signal in response to interruption of an optical beam 128 produced by a light source 130. The rejector trigger 126 is used to verify the position of a container 116 prior to rejecting the container 116. System operation is based on the assumption that there is no slippage (i.e., that a container's position on the conveyor does not change). Use of the rejector trigger 126 permits some container slippage, so long as a container does not slip by an entire container position (i.e., by the diameter of the container) between the location of the container trigger 122 and rejector trigger 126. As desired, the system may also include other optical sensors, including, for example, a fallen container sensor (not shown) and an optical sensor (not shown) that monitors the entrance of a rejection chute 132 for the passage of a container 116.

With reference also to FIGS. 2–5, inspection system 100 includes a cabinet 200 mounted on an adjustable stand 202. The cabinet 200 contains the x-ray source 102, the controller 106 and support electronics. The detector array 104 is mounted on an adjustable tunnel assembly 204 that is itself connected to the cabinet 200. The adjustable tunnel assembly also supports the optical container trigger 122. Accordingly, the system may be adjusted for a change in container size by adjusting the vertical position of the tunnel assembly 204. The position of the tunnel assembly 204 is controlled and monitored by the controller 106. Typically, the controller 106 can adjust the height of the tunnel assembly within a ten inch range, which permits the size of the containers to be varied between, for example, seven ounce cans and forty ounce bottles. The system could also be adjusted by automatically or mechanically adjusting the vertical position of the stand 202.

A user interface 206, including a video display 208 and input keys 210 is provided on the front of cabinet 200. A warning light 212 indicates that the system is operational. In addition to providing support for the source, detector, electronics and user interface, the cabinet 200 provides shielding to protect the system operator from exposure to x-ray radiation.

The support electronics include amplifiers that amplify the analog signals produced by the detector array 104 and power supplies for the system and x-ray source. The system also includes a slit assembly 402 (see FIG. 4) for collimating the x-ray beam produced by the x-ray source 102.

Figure 4:
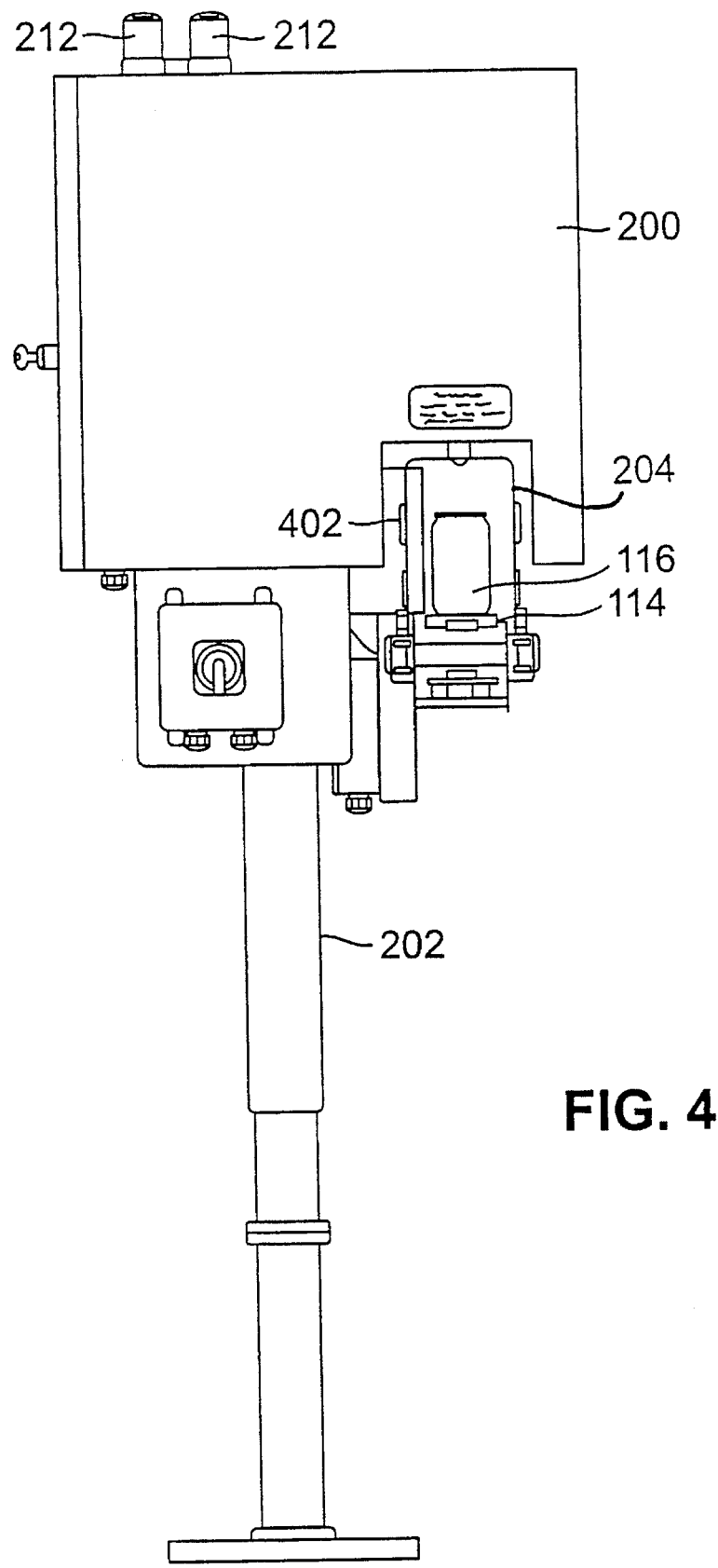
FIG. 4 is a side view of the container inspection system of FIG. 2, showing the side through which containers enter the container inspection system.
Figure 5:
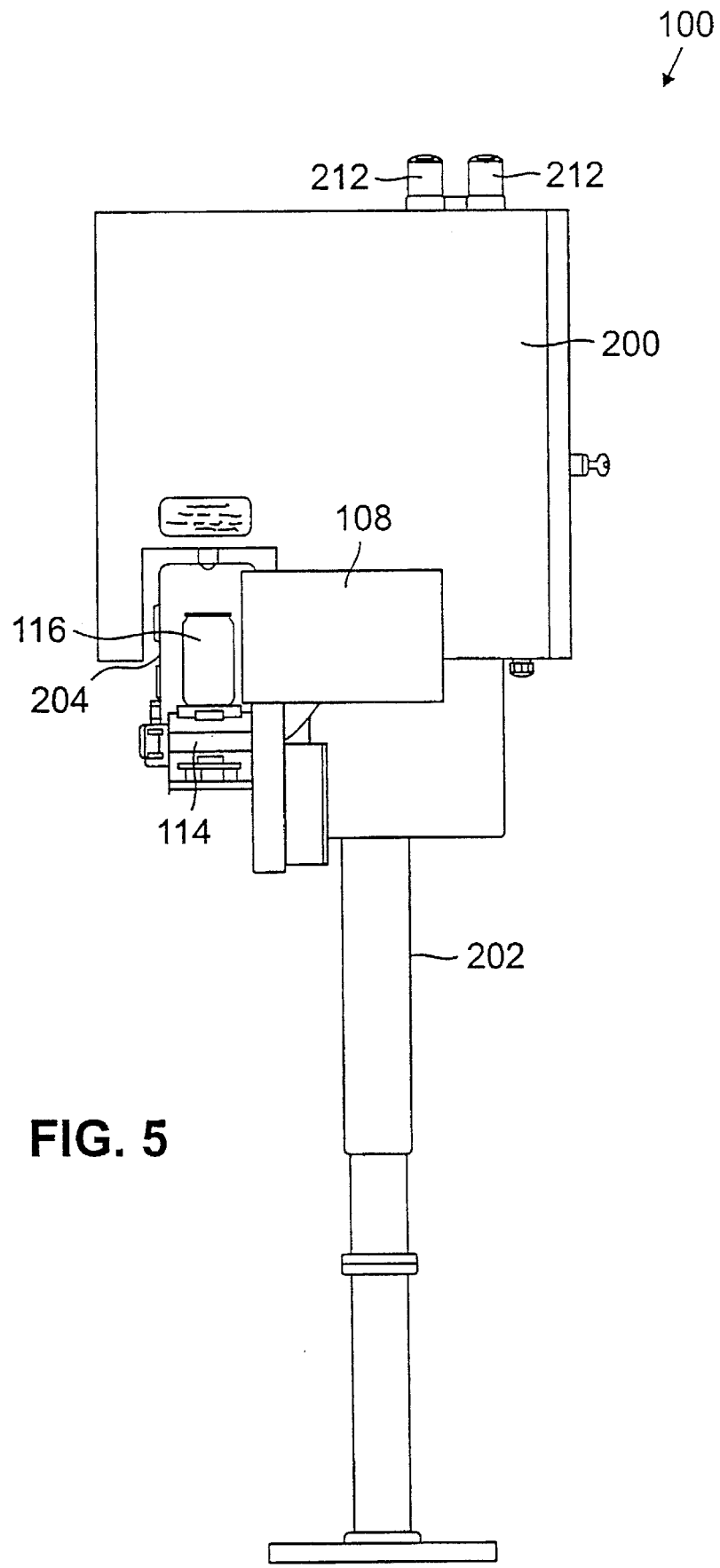
FIG. 5 is a side view of the container inspection system of FIG. 2, showing the side through which containers exit the container inspection system.

Alignment of the source 102, the beam 110 and the detector 104 is maintained through the connection of both the source 102 and the detector 104 to the cabinet 200. Accordingly, as best illustrated in FIG. 4, the system may be easily installed by positioning the system so that the tunnel assembly 204 straddles the conveyor 114 and is horizontally aligned with the conveyor 114. The system only needs to be roughly aligned in the vertical direction because, as discussed below, the vertical position of the tunnel assembly is automatically adjusted during an initialization procedure, which allows for quick changeover from one container size to another.

Figure 3:
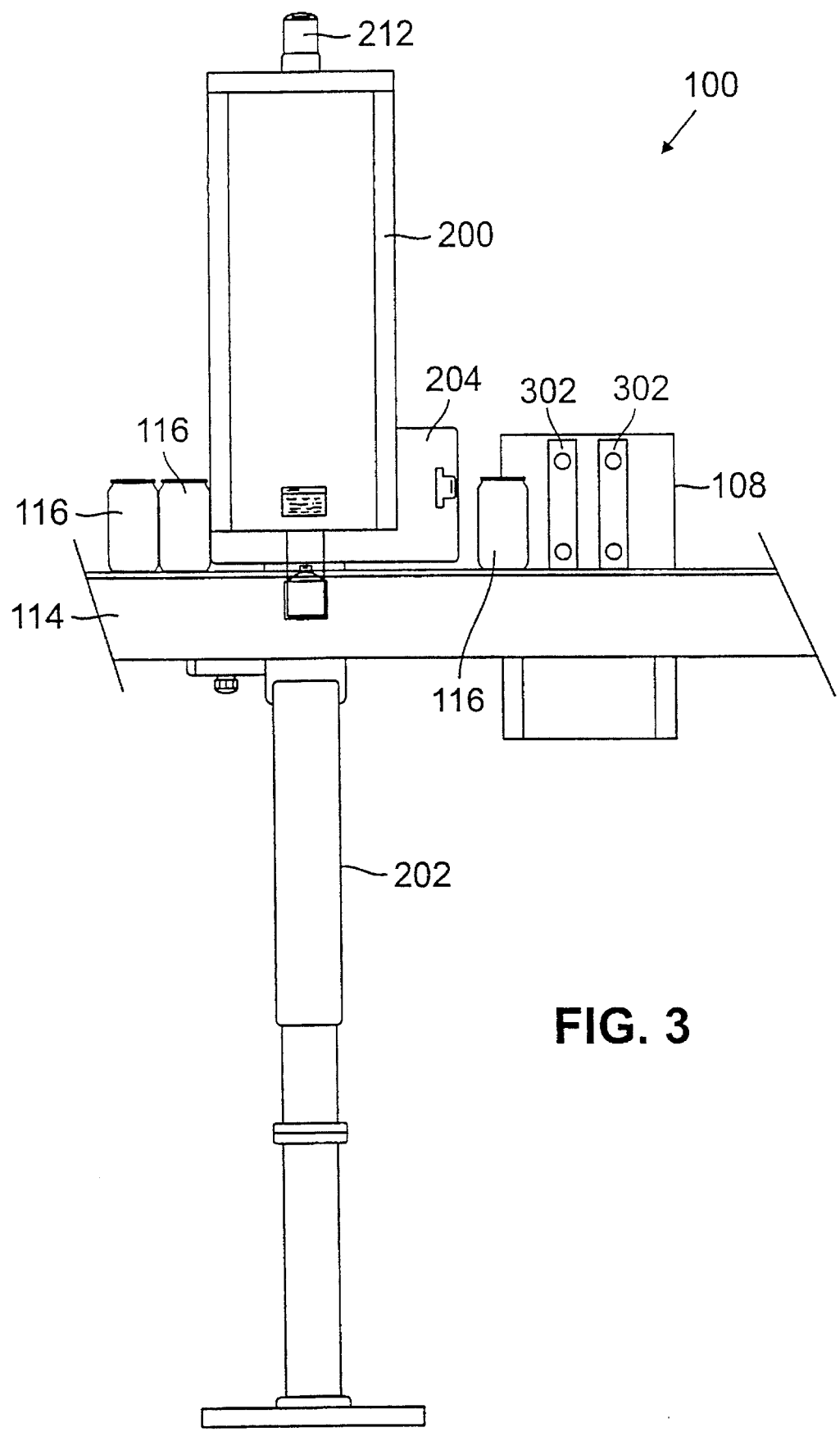
FIG. 3 is a rear view of the container inspection system of FIG. 2.

As illustrated in FIG. 3, the rejector 108 includes a pair of air-driven rams 302. Each ram 302 includes a solenoid and an air pressure cylinder, and is independently controlled by the controller 106. The use of two rejectors permits the rejection of containers 116 at conveyor speeds of up to 2400 containers per minute by alternating the duty cycle of each ram 302 as demanded by system reject conditions. Sensors (not shown) associated with each ram 302 monitor the condition of the ram by providing an indication of the time that the ram leaves its rest position and the time it returns. An optical sensor (not shown) that straddles the rejection chute 132 (FIG. 1) verifies that a desired container 116 has actually been rejected and detects any undesired rejections. Operation of the rejector 108 is completely automatic—the system tracks the position of a container 116 to be rejected, rejects the defective container, verifies the rejection and monitors the condition of the rejector ram 302.

The x-ray source 102 provides a continuous x-ray beam at 40–70 kV and 0.01 to 0.08 mA (i.e., 0.4–5.6 W). The power level is adjustable for different types of containers (e.g., aluminum versus steel) via jumpers on a control board within the cabinet 200. The power level may also be adjusted by the controller 106. Typically, the power level is roughly adjusted based on the type of container to be inspected and is fine-tuned thereafter to provide suitable contrast. The controller 106 monitors the operating power of the x-ray source. In the described embodiment, the x-ray source is supplied by Lorad Division, ThermoTrex Corporation, Danbury, Connecticut. Use of a continuous source eliminates timing problems associated with pulsed sources.

Figure 6:
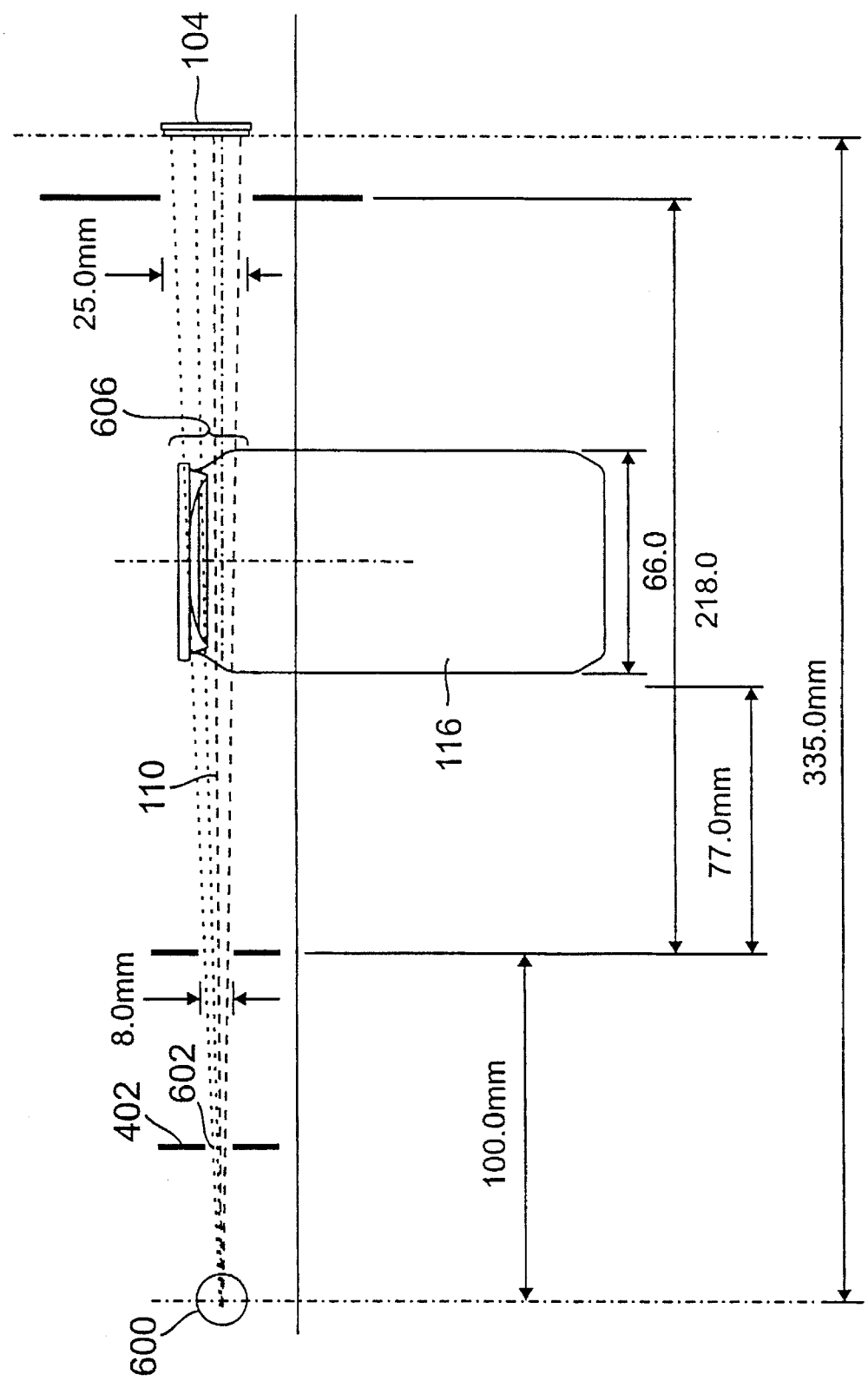
FIG. 6 is a plan view of the orientation of the x-ray source and x-ray detector of the container inspection system of FIG. 2 relative to a container.

As illustrated in FIG. 6, the x-ray source is a one millimeter spot source 600 that is collimated through the slit assembly 402 to produce the x-ray beam 110. The slit 602 of the slit assembly 402 is one millimeter wide and fifteen millimeters high. To increase the resolution of the system, an x-ray source having a smaller spot source could be used. As also illustrated in FIG. 6, the x-ray beam 110 is oriented so that it passes through only an upper portion 606 of the container 116. As discussed below, the x-ray absorption characteristics of this region of the container include all of the information necessary to determine whether the container is defective. Of course, if desired or necessary, the x-ray beam 110 could be oriented to produce an image of the entire container 116.

Figure 7:
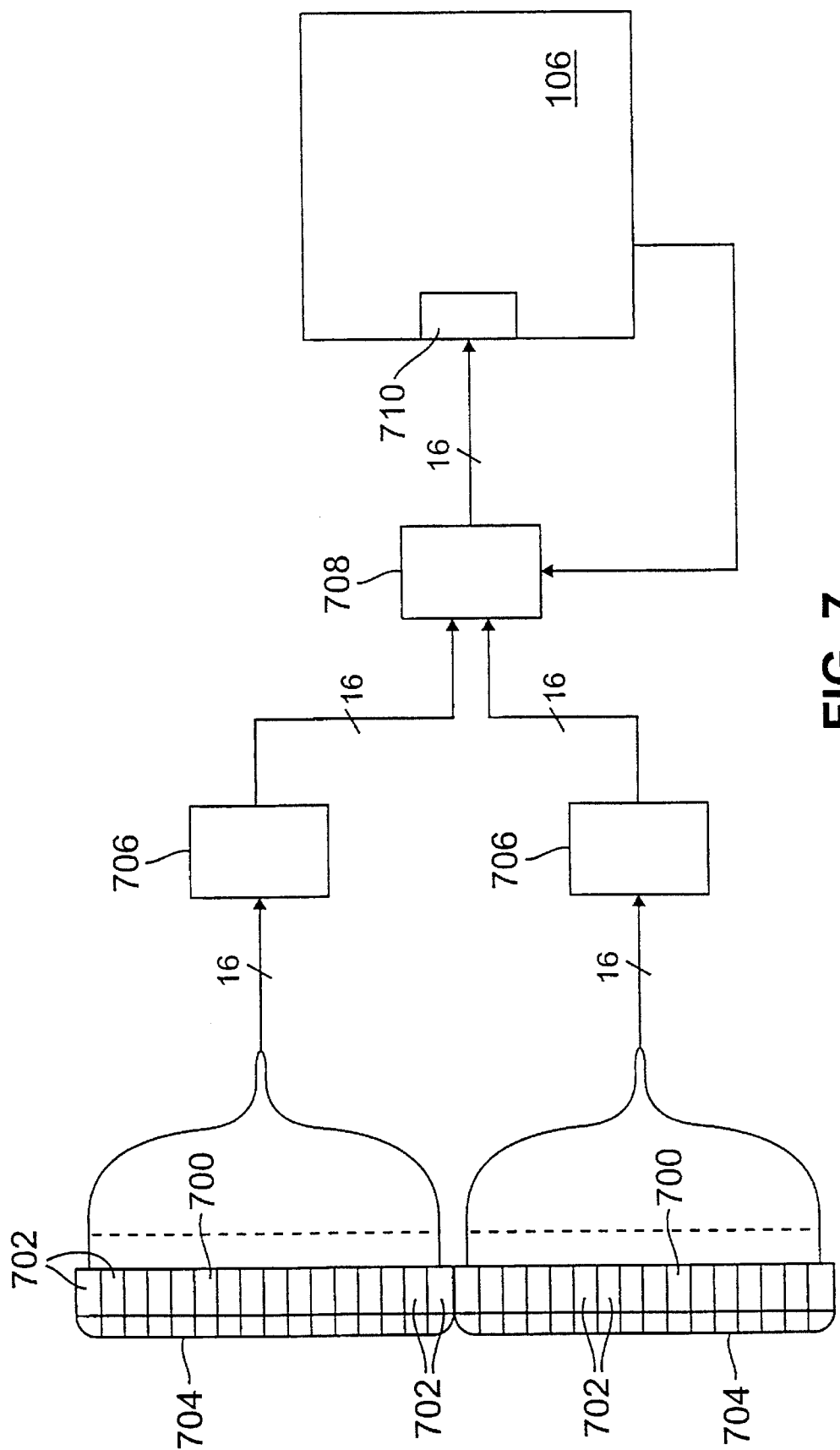
FIG. 7 is a block diagram of the detector and the controller of the container inspection system of FIG. 2.

As illustrated in FIG. 7, the detector array 104 includes two 16 element arrays 700. The photosensitive surface of each diode 702 of the arrays is two millimeters wide and one millimeter high, and the diodes 702 are enhanced for sensitivity to ultraviolet radiation. Though each diode is one millimeter high, the detector array provides vertical resolution on the order of 0.5 millimeters. This increase in resolution occurs because the beam is projected at an angle through the container and because a portion of the container positioned between the vertical centers of two adjacent diodes 702 will affect both of the diodes, and can therefore be identified by variations in the signals produced by the two diodes. A segmented cesium/iodide crystal scintillator 704 that converts incident x-ray radiation to ultraviolet radiation overlies each array 700. In the described embodiment, the arrays 700 are supplied by Photonics Corporation.

A phosphor screen could be substituted for the crystal scintillator 704. However, the scintillator may be preferred because it provides a quicker response; the use of a phosphor screen may also blur the image. In addition, an unsegmented phosphor screen would tend to increase crosstalk between the diodes.

The analog signal produced by each diode 702 is amplified by a dedicated amplifier on an amplifier board 706. The amplified signals are then supplied to a 32-to-16 multiplexer 708 that is controlled by a signal from the controller 106. The signals produced by the multiplexer are supplied to a sixteen bit analog input channel 710 of the controller 106. Each bit of the analog input channel is converted to a digital value with twelve bits of resolution. Typically, the controller 106 is implemented using an 80486 processor available from Intel Corporation.

Figure 8:
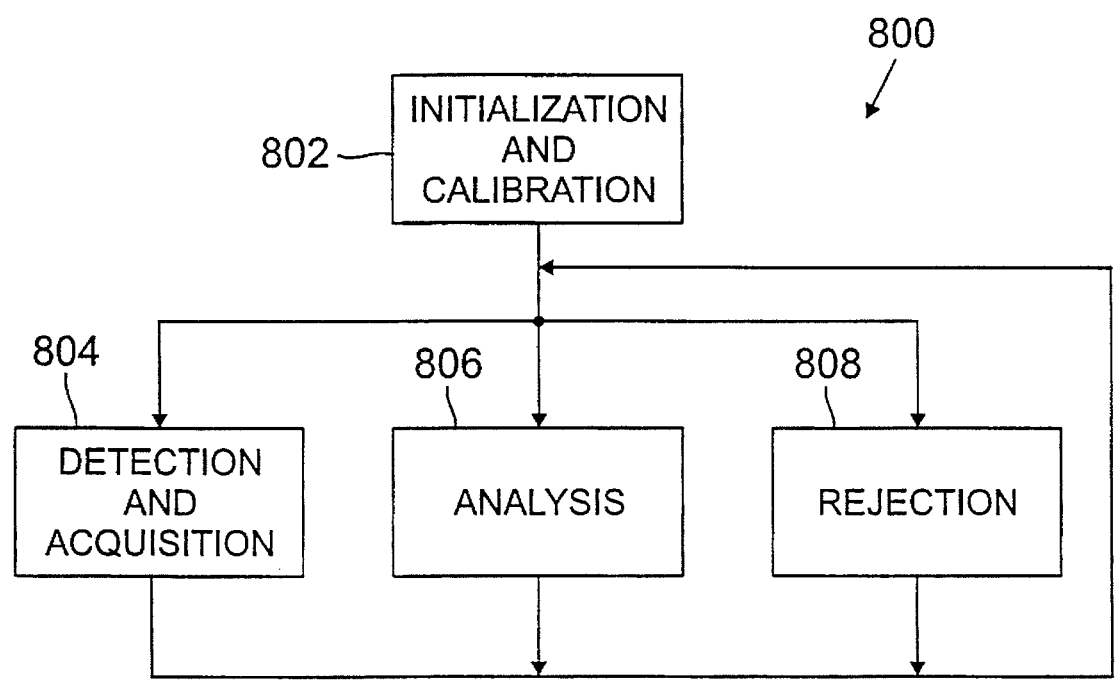
FIGS. 8–12 are flow charts of procedures implemented by the controller of the container inspection system of FIG. 2.

With reference to FIG. 8, controller 106 controls the system 100 according to a procedure 800. To begin system operation, a user selects initialization using the keypad 210 of the user interface 206 (see FIG. 1). In response, the controller 106 implements an initialization and calibration routine 802. After initialization, the controller operates the system according to a detection and acquisition routine 804 that detects a container 116 and acquires data for the container 116. Upon completion of that routine, the controller 106 operates the system according to an analysis routine 806 to determine whether the container is defective. If the controller 106 determines that the container 116 is defective, the controller operates the system according to a rejection routine 808. It is important to note that the system can simultaneously operate according to the detection, acquisition and rejection routines. For example, the system could operate to reject a first container at the same time that it is analyzing the data for a second container and acquiring data for a third container. In the described embodiment, the controller 106 is sufficiently fast to complete analysis of the data for one container while it is acquiring data for another container. Accordingly, the controller 106 includes two data buffers, each of which is of sufficient size to store the data for one container.

Figure 9:
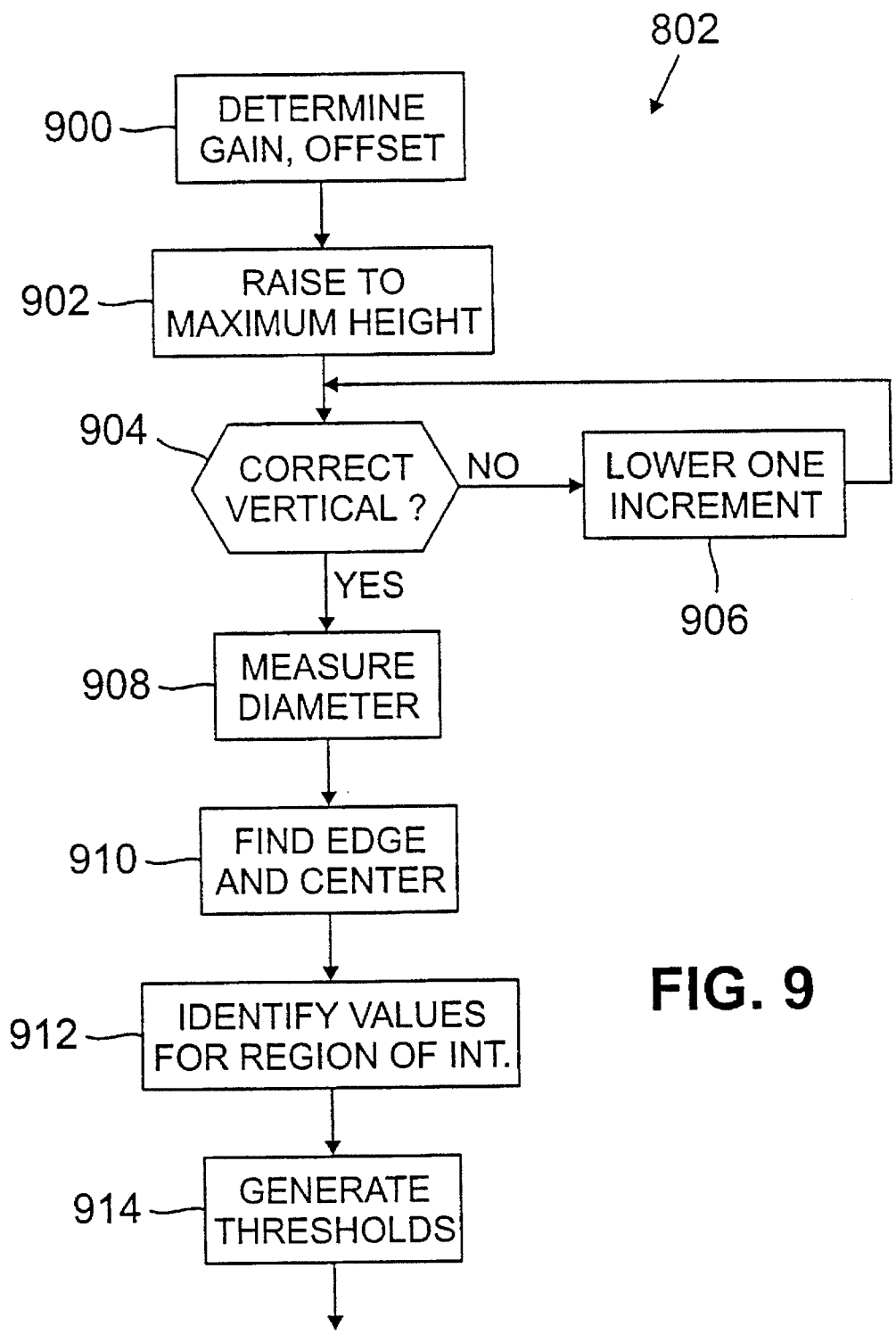

With reference to FIG. 9, controller 106 begins the initialization and calibration routine 802 by determining the gain and offset of each diode 702 of the detector array 104 (step 900). As is well known, the voltage produced by a diode 702 corresponds to the offset voltage of the diode plus the product of the x-ray radiation incident on the diode and the gain of the diode:

V=gain* incident+offset.

Accordingly, when the gain and offset of a diode are known, the x-ray radiation incident on the diode can be determined from the voltage produced by the diode. Because the gains and offsets vary from diode to diode, the controller 106 determines and stores the gain and offset for each diode, and uses these values when processing the signals produced by the diodes. Controller 106 determines the offset of each diode by measuring the voltage produced by each diode when the x-ray source 102 is disabled so that no x-ray radiation is incident on the diode:

$$V = gain* 0 + offset = offset.$$

Once the offsets are known, the processor determines the gain of each diode by subtracting the offset of the diode from the voltage produced by the diode when the x-ray source 102 is turned on and no container interrupts the x-ray beam 110:

$$V - offset = gain* 1 = gain,$$

where the incident x-ray radiation is normalized so that a value of 1 corresponds to an uninterrupted beam and a value of 0 corresponds to no incident radiation.

Next, the controller 106 controls the adjustable stand 202 to raise the system to its highest vertical position (step 902) and prompts the system operator (via user interface 206) to place a test container on the conveyor 114. Thereafter, the controller 106 monitors the signals produced by the detector array 104 to determine whether the vertical position of the system is correct (step 904). In the described embodiment, the correct vertical position is defined as the position in which the x-ray radiation incident on the fifth diode 702 from the top of the detector array 104 is less than or equal to 70% of a full beam (i.e., the test container blocks at least 30% of x-ray radiation directed to that diode). If the vertical position is not correct, the controller 106 instructs the adjustable stand 202 to lower the system by one increment (step 906) and checks the position again.

Once the vertical position of the system is correct, the controller prompts the operator to place the test container on the conveyor and measures the diameter of the test container (step 908). In the described embodiment, the controller 106 measures the diameter of the container relative to the speed of the conveyor 114 by counting the number of pulses produced by the encoder 124 from the time that the test container interrupts the optical beam 118 and activates container trigger 122 until the time that the test container passes out of the optical beam 118 and deactivates container trigger 122. At the same time, the controller 106 determines the relationship between the encoder pulses and horizontal distance by counting the number of encoder pulses that occur between activation of the container trigger 122 by the test container and activation of the rejector trigger 126 by the test container. Because the distance between these triggers is known, the distance per encoder pulse can be determined by dividing the known distance by the pulse count.

Next, the controller 106 identifies the edge and center of the test container (step 910). Once the test container interrupts the optical beam 118, the controller 106 stores the values of the signals produced by each diode 702 for successive horizontal increments (typically on the order of every other encoder pulse). Based on these values, the controller 106 identifies the edge of the test container as corresponding to the first set of signals in which a portion of the x-ray radiation incident on the fifth diode 702 from the top of the diode array is interrupted by the test container. After identifying the edge of the test container, the controller 106 identifies the center of the test container as corresponding to the set of signals spaced from the edge by one half of the number of encoder pulses corresponding to the diameter of the container.

Figure 13:
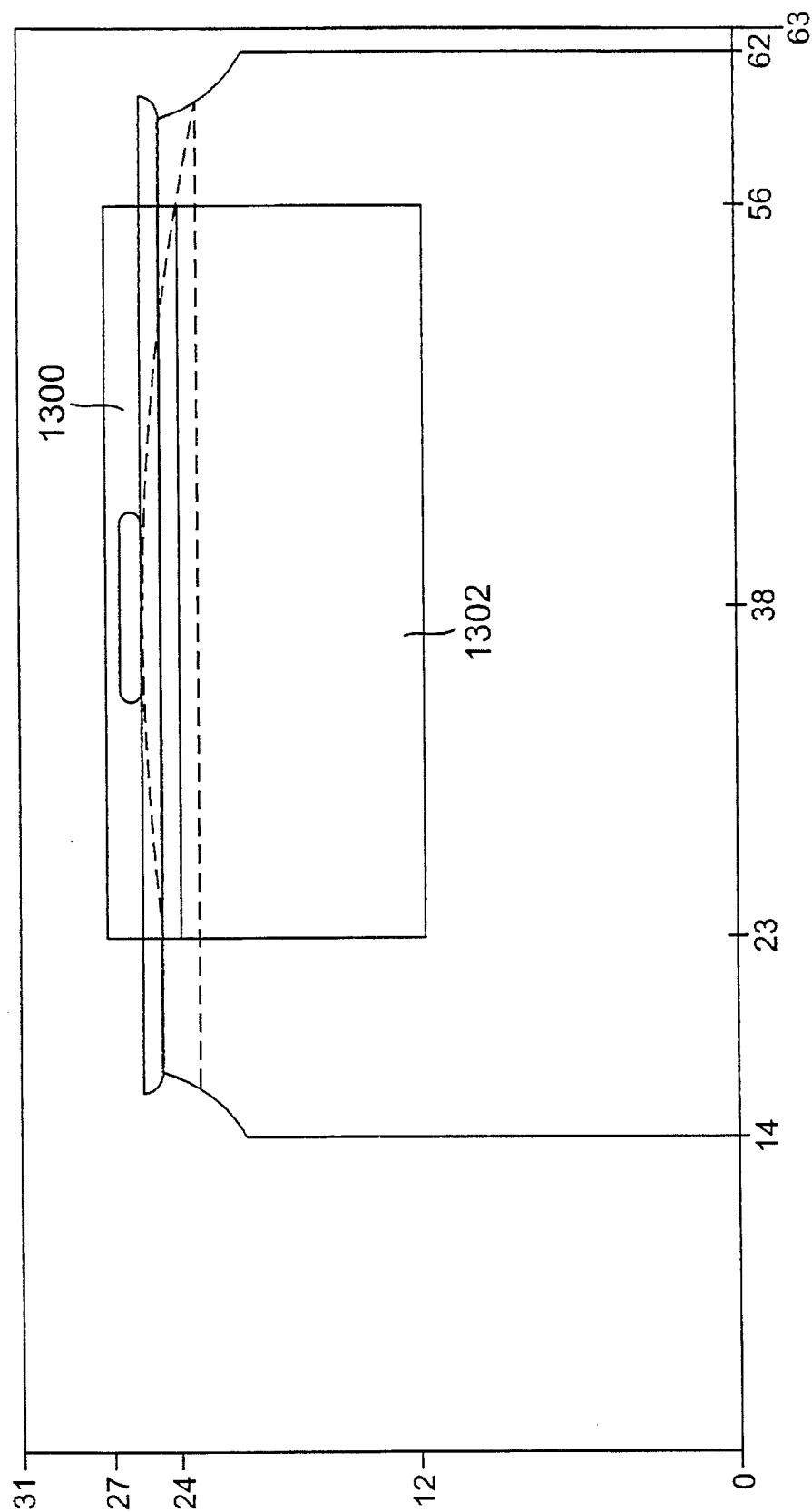
FIG. 13 is a graphical view of image data produced by the container inspection system of FIG. 2.

Once the edge and center of the test container have been identified, the controller 106 identifies the values corresponding to the regions of the image that are of particular interest. As illustrated in FIG. 13, in the described embodiment, where the containers are beverage cans, the image data includes 64 columns of data, each of which includes 32 entries (corresponding to the 32 diodes of the diode array). The leading edge of the can occurs at column 12, and the center of the can occurs at column 38. There are two regions of interest. The first region 1300, which corresponds to the top of the can and is used in determining whether the can is properly pressurized, includes columns 35 to 41 of rows 24 to 27. The second region 1302 is used in measuring the liquid level in the can and includes columns 23 to 56 of rows 12 to 23.

Finally, using the values corresponding to the regions of interest, the controller 106 generates threshold values for each region of interest (step 914). For the first region 1300, the tab of the can top is expected to be positioned in the center of the region. Accordingly, the controller 106 multiples the values corresponding to rows 26 and 27 by a positive weighing factor, multiplies the values corresponding to rows 24 and 25 by a negative weighing factor, and adds all of the values together to produce the threshold value.

For the second region 1302, the controller 106 adds all of the values together to produce the threshold value. By adding all of the values together, the controller 106 generates a measure of the x-ray absorption properties of the entire second region 1302. This is extremely significant because it results in the system's ability to measure fill level being insensitive to agitation of the contents of the container. In the prior art, fill level sensors typically had to be placed at least 15–30 feet downstream of a source of agitation such as a conveyor curve or a filling station to permit the contents of the containers to settle prior to analysis. By contrast, the container inspection system 100 may be placed on a curve or immediately after a source of agitation without detrimental results.

Figure 10:
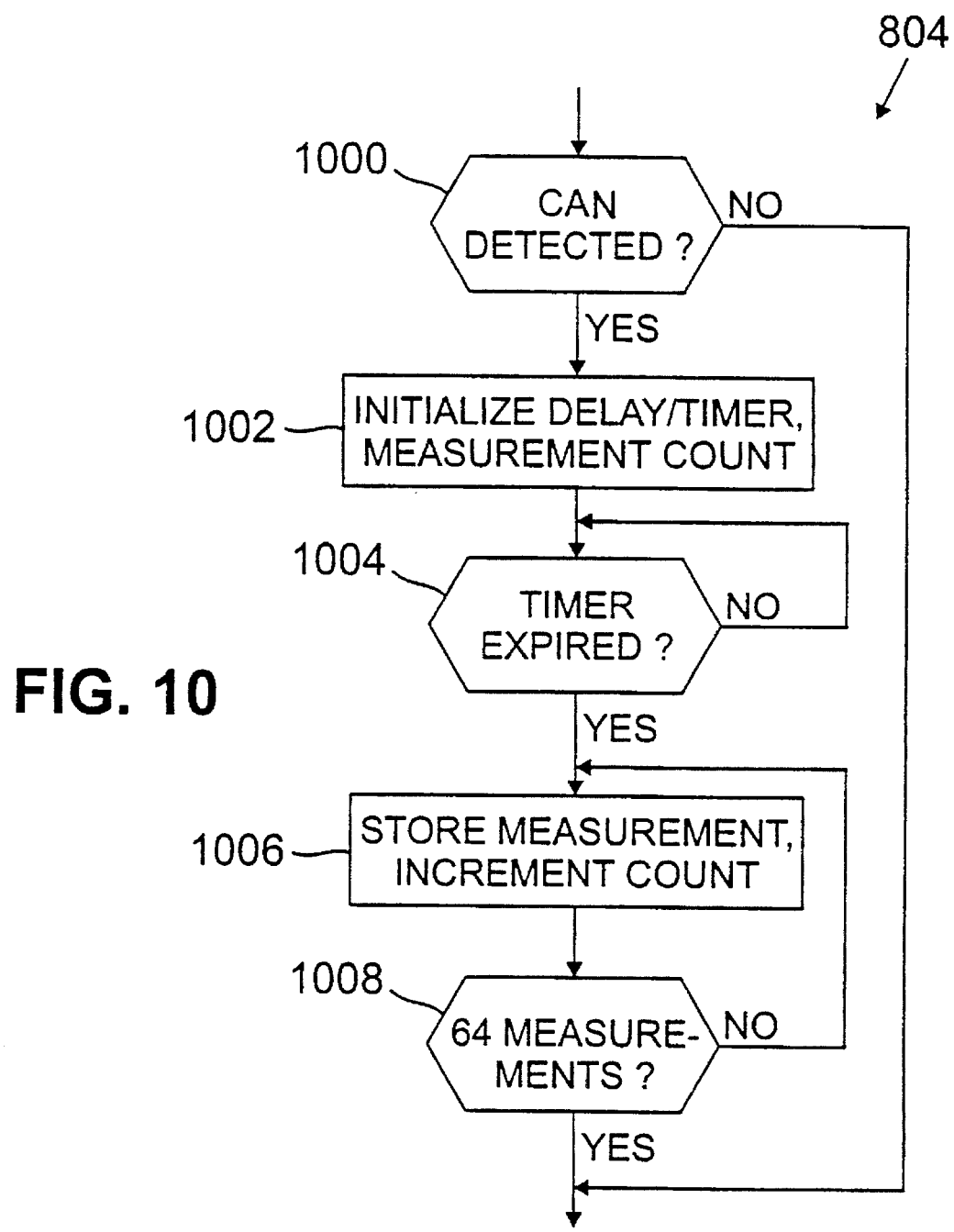

With reference to FIG. 10, the controller 106 begins the detection and acquisition routine 804 by determining whether the container trigger 122 has detected a container (step 1000). If so, the controller 106 initializes a delay/timer to a value corresponding to the number of encoder pulses that are expected to occur before the leading edge of the container is properly positioned, and initializes a measurement count to zero (step 1002). Thereafter, the controller monitors the encoder pulses until the delay/timer expires (step 1004).

After the delay/timer expires, the controller 106 stores measurement values from the diode array and increments the measurement count (step 1006). As discussed above, the measurement values are generated by modifying the number corresponding to the voltage of each diode by the offset and gain of that diode. If 64 measurements have not been taken (step 1008), the controller waits for the occurrence of a proper number of encoder pulses and repeats the storing and incrementing step (step 1006). Once 64 measurements are taken, the controller 106 begins the analysis routine 806 and simultaneously starts the detection and acquisition routine for the next container 116.

Figure 11:
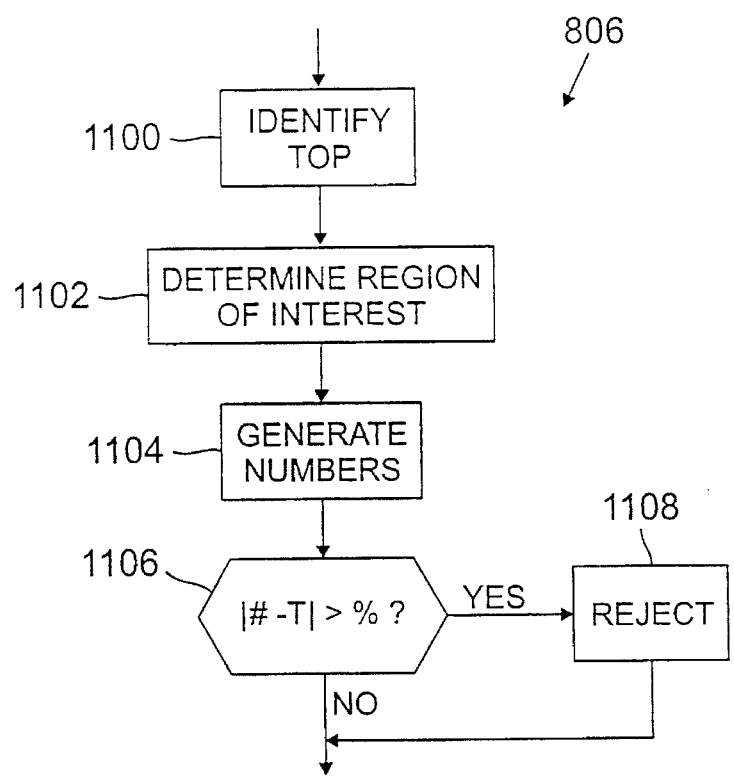

With reference to FIG. 11, controller 106 begins the analysis routine 806 by identifying the position of the top of the container within the measured data (step 1100). By permitting the position of the top of the container to vary, the controller 106 accounts for variations in the height of the conveyor that could result, for example, from unevenly worn components in the conveyor.

Once the top of the container is identified, the controller determines the regions of interest for the container (step 1102). As discussed above the top of the test container is positioned at row 28 (i.e., at the fourth diode from the top), and the first region 1300 is defined at rows 24 to 27. Thus, if the top of the container were identified at row 29, the first region 1300 would be defined at rows 25 to 28.

After identifying the regions of interest, the controller 106 generates numbers for each region of interest using the procedure described above for generating the thresholds (step 1104). These numbers are then compared to the thresholds (step 1106). If one of the numbers varies from the corresponding threshold by a predetermined percentage, the controller 106 determines that the container should be rejected (step 1108). When the controller 106 determines that a container should be rejected, the controller executes the rejection routine 808.

Figure 12:
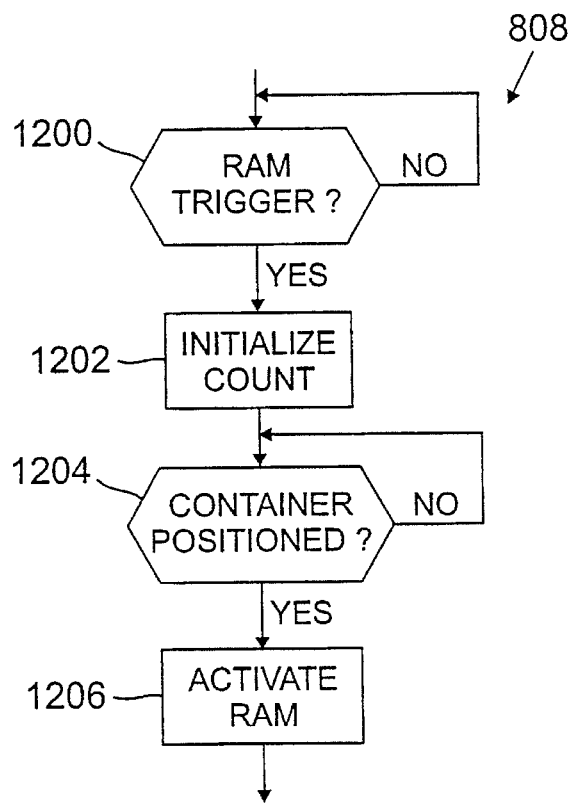

With reference to FIG. 12, the controller 106 begins the rejection routine 808 by waiting for the container to interrupt the optical beam 128 of the rejector trigger 126 (step 1200). When this occurs, the controller 106 knows the exact position of the container and responds by initializing a counter that counts pulses from the encoder 124 (step 1202). The controller 106 then counts the pulses until the count indicates that the container is positioned so that a rejector ram 302 should be activated (1204). Thereafter, the controller activates the rejector ram 302. As noted above, the controller 106 activates the rejector rams 302 in an alternating manner. As such, the pulse count that is indicative of proper container position will vary based on which of the rejector rams 302 is to be activated. It is also important to note that, due to the speed of the conveyor 104 relative to the speed of the rejector rams 302, a rejector ram 302 will typically be activated before the container is positioned in front of the rejector ram, and a signal to return the rejector ram to its rest position may be issued before the container reaches the ram. The controller 106 modifies the pulse count corresponding to proper container position based on feedback signals received from the rejector rams. This permits the controller 106 to account for changes in the operating characteristics of the rejector rams over time.

Figure 14:
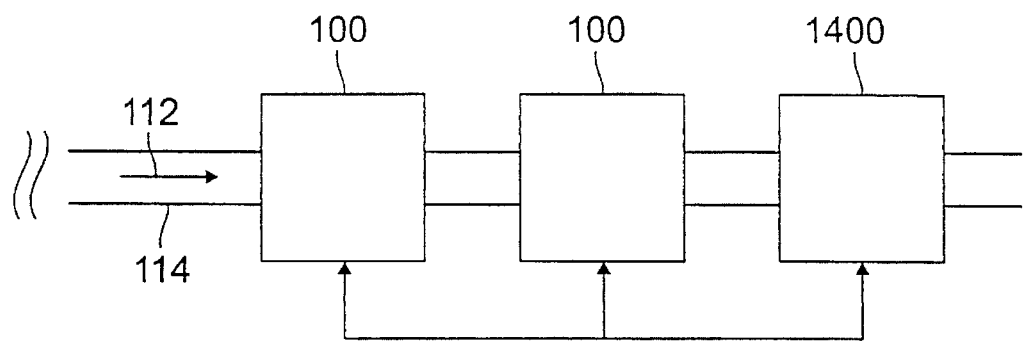
FIGS. 14–16 are block diagrams showing positioning of a container inspection system.

As illustrated in FIG. 14, two or more inspection systems 100 can be employed to provide failsafe operation. When two inspection systems 100 are employed, the systems are positioned sequentially along conveyor 114 and share a common rejector 1400 that is positioned downstream of the systems relative to the direction of motion 112 of the conveyor. With this arrangement, each system 100 inspects every container and rejects containers that it finds to be defective. Each system 100 monitors the signals sent to the rejector 1400 by the other system 100 and compares the signals to those that it generates to verify proper system operation and detect system failure.

Figure 15:
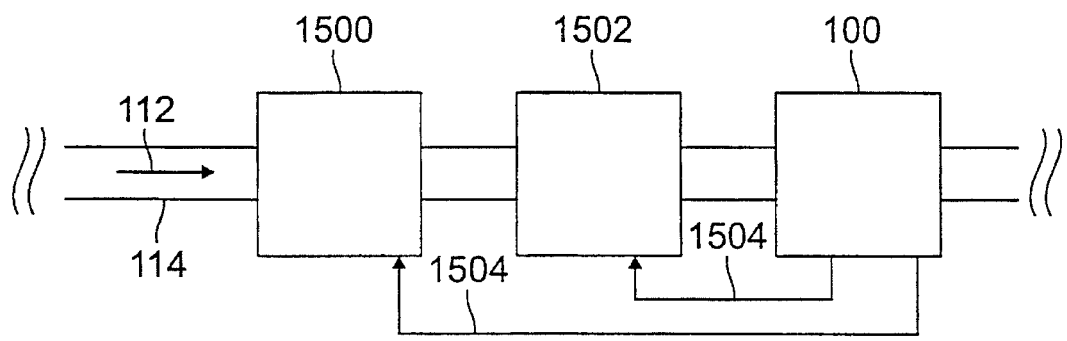

As illustrated in FIG. 15, the container inspection system 100 is typically positioned downstream, relative to the direction of movement 112 of the conveyor 114, of a filler 1500 that fills the containers and a seamer 1502 that seals the containers. Feedback paths 1504 from the system 100 to the filler 1500 and seamer 1502 permit automatic adjustment of those components. For example, the filler 1500 may adjust a fill valve in response to information from system 100 which indicates that the fill valve is not operating properly. Similarly, seamer 1502 may make adjustments in response to information indicative of improperly sealed containers.

Figure 16:
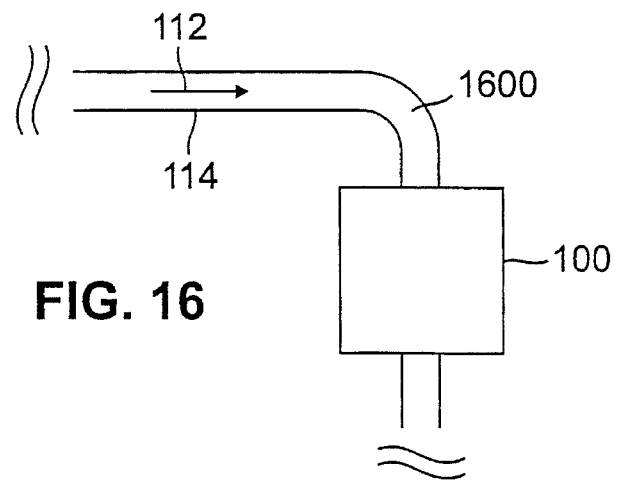

Finally, as illustrated in FIG. 16, the ability of the container inspection system 100 to accurately determine container fill level permits the system to be positioned immediately downstream of a curve 1600 in the conveyor 114.

Other embodiments are within the following claims. For example, to improve resolution, the x-ray beam 110 could be focused using, e.g., a tungsten honeycomb structure, or the number of elements in the detector array could be increased. Similarly, a detector array having higher element density in a region of particular interest could be employed. In addition, the x-ray source could be replaced with a source of gamma radiation. However, x-ray radiation is preferred over gamma radiation because, for a particular power level, x-ray radiation provides more information.

While the system described above is configured primarily for inspecting cans that are expected to have nearly identical characteristics, it could also be used to inspect bottles or other containers in which the wall thickness of the container varies from container to container or even within a given container. When inspecting such variable containers, the system would determine the wall thickness of each container and account for the effects of variations in that thickness. In addition, unlike cans, filled bottles typically include a large headspace in which varying levels of foam may form. To determine whether a bottle is properly filled, the system would detect a level of foam in the bottle and, based on the density of the foam, modify the measured liquid level accordingly.

In one approach to analyzing foam, the controller 106 searches for positive gradients in x-ray attenuation between horizontal rows of a region of interest in the image data. The controller uses the location of these gradients to determine the relative position of the foam-liquid boundary. Once the boundary has been located, the controller determines the volume of the foam based on the known geometry of the container and assuming that the foam fills the entire container volume above the foam-liquid boundary. The controller determines the density of the foam by comparing absorption measurements from detector elements immediately above and below the boundary, where the measurement from below the boundary corresponds to the absorption by liquid and the measurement from above the boundary corresponds to the absorption by foam. Thereafter, the controller determines the amount of liquid in the foam by multiplying the volume of foam by the density of the foam. Finally, the controller adjusts the measured fill level in accordance with this amount.

Where appropriate, an air/foam boundary could also be detected, and its position could be used in determining the volume of foam in the container.

When examining a glass container, the controller estimates the thickness of the container's walls by measuring the attenuation gradient along the vertical edges of the container. The controller may use the glass thickness as a first order correction for the volume of the container in both the fill level and foam measurements.

In another approach to analyzing the image data, image data for the regions of interest for a large number (e.g., 100 to 1000) of containers could be used to train a neural network. Thereafter, containers could be inspected by applying their image data to the neural network.

What is claimed is:

1. A system for determining fill level or pressurization of a moving container, comprising:

a radiation source positioned to direct radiation at the moving container;

a radiation detector positioned to receive a portion of the radiation from the radiation source that is not absorbed or blocked by the moving container and to generate electrical signals in response thereto; and processing circuitry operable to:

produce multi-dimensional image data for the moving container based on the electrical signals generated by the radiation detector, compare at least a first portion of the multi-dimensional image data to a corresponding portion of the multi-dimensional image data for a standard container, and determine, based on a result of the comparison, one or more characteristics of the container from the set of characteristics including the fill level of the container, whether the container is underfilled, whether the container is overfilled, whether the container is properly pressurized, and whether the container is sealed.

2. The system of claim 1, wherein said processing circuitry is operable to determine that the moving container differs from the standard container when the portion of the multi-dimensional image data for the moving container differs from the portion of the multi-dimensional image data for the standard container by more than a predetermined amount.

3. The system of claim 2, wherein each of the first portion and the corresponding portion includes a plurality of elements, and wherein said processing circuitry is operable to combine values associated with each of the plurality of elements of the first portion to produce a first composite value, to combine values associated with each of the plurality of elements of the corresponding portion to produce a second composite value, and to compare the first and second composite values to determine the characteristic of the container.

4. The system of claim 3, wherein the first portion includes multi-dimensional image data corresponding to a region above and below an expected fill level in the moving container and wherein the processing circuitry is operable to determine an actual fill level of the container as the characteristic of the container.

5. The system of claim 4, further comprising a rejector, wherein the processing circuitry is operable to activate the rejector when the fill level of the container differs from a fill level of the standard container by more than a predetermined amount.

6. The system of claim 3, wherein the first portion includes multi-dimensional image data corresponding to a region that includes a top surface of the container and wherein the processing circuitry is operable to determine whether the moving container is properly pressurized as the characteristic of the container.

7. The system of claim 1, wherein the radiation detector comprises a one-dimensional, linear detector array operable to produce electrical signals corresponding to a one-dimensional segment of the moving container, and the processing circuitry is operable to produce the multi-dimensional image data by assembling sets of electrical signals corresponding to one-dimensional segments of the moving container.

8. The system of claim 7, wherein:

the moving container moves in a horizontal direction, the radiation detector comprises a one-dimensional, vertical, linear detector array, and the radiation detector is operable to generate the sets of electrical signals as the container moves past the detector array.

9. The system of claim 1, wherein the radiation source is operable to direct radiation at only an upper portion of the moving container.

10. The system of claim 1, wherein:

the moving container comprises a can having contents sealed therein, the first portion of the multi-dimensional image data corresponds to a region at the top of the can, and the processing circuitry is operable to determine that the moving container is not properly pressurized when the multi-dimensional image data for the region at the top of the can differs from the multi-dimensional image data for the region at the top of the standard container.

11. The system of claim 1, wherein the radiation source comprises a continuous x-ray source.

12. The system of claim 1, further comprising a mechanism operable to automatically adjust the vertical position of the radiation source and the radiation detector based on the height of the moving container.

13. The system of claim 1, wherein the moving container is positioned on a conveyor, the system further comprising a rejector operable to remove the moving container from the conveyor when the processing circuitry determines that the moving container differs from the standard container.

14. The system of claim 13, wherein the rejector comprises an air-driven ram.

15. The system of claim 14, wherein the rejector comprises a pair of air-driven rams operable in an alternating manner.

16. The system of claim 14, wherein the rejector is operable to provide to the processing circuitry information about movement of the air-driven ram.

17. A system for inspecting a moving container, comprising:

a radiation source positioned to direct radiation at the moving container;

a radiation detector positioned to receive a portion of the radiation from the radiation source that is not absorbed or blocked by the moving container and to generate electrical signals in response thereto; and processing circuitry operable to:

produce multi-dimensional image data for the moving container based on the electrical signals generated by the radiation detector, compare at least a first portion of the multi-dimensional image data to a corresponding portion of the multi-dimensional image data for a standard container, and determine a fill level of the container based on a result of the comparison.

18. The system of claim 17, wherein said processing circuitry is operable to determine that the moving container differs from the standard container when the portion of the multi-dimensional image data for the moving container differs from the portion of the multi-dimensional image data for the standard container by more than a predetermined amount.

19. The system of claim 18, wherein each of the first portion and the corresponding portion includes a plurality of elements, and wherein said processing circuitry is operable to combine values associated with each of the plurality of elements of the first portion to produce a first composite value, to combine values associated with each of the plurality of elements of the corresponding portion to produce a second composite value, and to compare the first and second composite values to determine the characteristic of the container.

20. The system of claim 19, wherein the first portion includes multi-dimensional image data corresponding to a region above and below an expected fill level in the moving container.

21. The system of claim 20, further comprising a rejector, wherein the processing circuitry is operable to activate the rejector when the fill level of the container differs from a fill level of the standard container by more than a predetermined amount.

22. The system of claim 19, wherein the first portion includes multi-dimensional image data corresponding to a region that includes a top surface of the container and wherein the processing circuitry is operable to determine whether the moving container is properly pressurized.

23. The system of claim 17, wherein the processing circuitry is operable to determine whether the container is underfilled, whether the container is overfilled, whether the container is properly pressurized, whether the container is sealed, whether the container includes a properly positioned lid, whether the container includes a properly positioned tab.

24. The system of claim 17, wherein the radiation detector comprises a one-dimensional, linear detector array operable to produce electrical signals corresponding to a one-dimensional segment of the moving container, and the processing circuitry is operable to produce the multi-dimensional image data by assembling sets of electrical signals corresponding to one-dimensional segments of the moving container.

25. The system of claim 24, wherein:

the moving container moves in a horizontal direction, the radiation detector comprises a one-dimensional, vertical, linear detector array, and the radiation detector is operable to generate the sets of electrical signals as the container moves past the detector array.

26. The system of claim 24, wherein the radiation detector comprises an array of photodiodes.

27. The system of claim 17, wherein the radiation source is operable to direct radiation at only an upper portion of the moving container.

28. The system of claim 17, wherein:

the moving container comprises a can having contents sealed therein, the first portion of the multi-dimensional image data corresponds to a region at the top of the can, and the processing circuitry is operable to determine that the moving container is not properly pressurized when the multi-dimensional image data for the region at the top of the can differs from the multi-dimensional image data for the region at the top of the standard container.

29. The system of claim 17, wherein the radiation source comprises a continuous x-ray source.

30. The system of claim 17, further comprising a mechanism operable to automatically adjust the vertical position of the radiation source and the radiation detector based on the height of the moving container.

31. The system of claim 17, wherein the moving container is positioned on a conveyor, the system further comprising a rejector operable to remove the moving container from the conveyor when the processing circuitry determines that the moving container differs from the standard container.

32. The system of claim 31, wherein the rejector comprises an air-driven ram.

33. The system of claim 32, wherein the rejector comprises a pair of air-driven rams operable in an alternating manner.

34. The system of claim 32, wherein the rejector is operable to provide to the processing circuitry information about movement of the air-driven ram.

35. A method of inspecting a moving container, comprising:

directing radiation at the moving container;

receiving a portion of the radiation that is not absorbed or blocked by the moving container;

producing multi-dimensional image data for the moving container based on the received radiation that was not absorbed or blocked by the moving container;

comparing at least a first portion of the multi-dimensional image data to a corresponding portion of the multi-dimensional image data for a standard container; and determining a fill level of the moving container based on a result of said step of comparing.

36. The method of claim 35, further comprising determining that the moving container differs from the standard container when the portion of the multi-dimensional image data for the moving container differs from the portion of the multi-dimensional image data for the standard container by more than a predetermined amount.

37. The method of claim 35, further comprising:

directing radiation at the standard container so that a portion of the radiation is absorbed or blocked by the standard container and a portion of the radiation is not absorbed or blocked by the standard container;

receiving the portion of the radiation that is not absorbed or blocked by the standard container; and producing the multi-dimensional image data for the standard container based on the received radiation that was not absorbed or blocked by the standard container.

38. The method of claim 35, wherein:

the step of receiving radiation comprises receiving radiation as a series of one-dimensional segments, and the step of producing the multi-dimensional image data comprises producing a set of one-dimensional image data from each of the one-dimensional segments of received radiation and assembling the sets of one-dimensional image data to produce the multi-dimensional image data.

39. The method of claim 38, further comprising moving the moving container in a horizontal direction, wherein the step of receiving radiation comprises receiving radiation as a series of one-dimensional, vertical segments as the moving container moves past a vertical detector.

40. The method of claim 35, wherein the step of directing radiation comprises directing radiation at only an upper portion of the moving container.

41. The method of claim 35, wherein:

the moving container comprises a can, the first portion of the multi-dimensional image data corresponds to a region at the top of the can, and the step of determining comprises determining that the moving container is not properly pressurized when the multi-dimensional image data for the region at the top of the can differs from the multi-dimensional image data for the region at the top of the standard container.

42. The method of claim 35, wherein the radiation comprises a continuous beam of x-ray radiation.

43. The system of claim 4, wherein the processing circuitry is operable to account for foam in the container when determining the actual fill level of the container.

44. The system of claim 43, wherein the processing circuitry is operable to determine an apparent fill level of the container, to determine a level of liquid attributable to foam in the container, and to combine the apparent fill level and the level attributable to foam to determine the actual fill level.

45. The system of claim 44, wherein the processing circuitry is operable to determine an amount of foam in the container, to determine a density of foam in the container, and to determine the level of liquid attributable to foam based on the amount of foam and the density of foam.

46. The system of claim 45, wherein the processing circuitry is operable to identify a foam/liquid interface and to determine the amount of foam in the container based on the foam/liquid interface and a geometry of the container.

47. The system of claim 46, wherein the processing circuitry is operable to identify an air/foam interface and to determine the amount of foam in the container based on the foam/liquid interface, the air/foam interface, and the geometry of the container.

48. The system of claim 45, wherein the processing circuitry is operable to determine a thickness of walls of the container and to determine that amount of foam in the container based on the thickness of walls of the container.

49. The system of claim 4, wherein the processing circuitry is operable to determine a thickness of walls of the container and to account for the thickness of walls of the container in determining the actual fill level of the container.

50. The system of claim 49, wherein the processing circuitry is operable to account for variations in a volume of the container due to the thickness of walls of the container.

51. The system of claim 4, wherein the processing circuitry is operable to account for movement of container contents when determining the actual fill level of the container.

52. The system of claim 1, wherein the processing circuitry is operable to determine a thickness of walls of the container.

53. The system of claim 52, wherein the processing circuitry is operable to account for variations in a volume of the container due to the thickness of walls of the container.

54. The system of claim 1, wherein the processing circuitry is operable to account for movement of container contents when determining the one or more characteristics of the container.

55. The system of claim 6, wherein the processing circuitry is operable to determine whether the moving container is properly pressurized when the moving container is in a non-inverted orientation.

56. The system of claim 17, wherein the processing circuitry is operable to account for foam in the container when determining the fill level of the container.

57. The system of claim 56, wherein the processing circuitry is operable to determine an apparent fill level of the container, to determine a level of liquid attributable to foam in the container, and to combine the apparent fill level and the level attributable to foam to determine the fill level.

58. The system of claim 57, wherein the processing circuitry is operable to determine an amount of foam in the container, to determine a density of foam in the container, and to determine the level of liquid attributable to foam based on the amount of foam and the density of foam.

59. The system of claim 58, wherein the processing circuitry is operable to identify a foam/liquid interface and to determine the amount of foam in the container based on the foam/liquid interface and a geometry of the container.

60. The system of claim 59, wherein the processing circuitry is operable to identify an air/foam interface and to determine the amount of foam in the container based on the foam/liquid interface, the air/foam interface, and the geometry of the container.

61. The system of claim 58, wherein the processing circuitry is operable to determine a thickness of walls of the container and to determine the amount of foam in the container based on the thickness of walls of the container.

62. The system or claim 17, wherein the processing circuitry is operable to determine a thickness of walls or the container and to account for the thickness of walls of the container in determining the actual fill level of the container.

63. The system of claim 62, wherein the processing circuitry is operable to account for variations in a volume of the container due to the thickness of walls of the container.

64. The system of claim 17, wherein the processing circuitry is operable to account for movement of container contents when determining the actual fill level of the container.

65. The system of claim 28, wherein the processing circuitry is operable to determine that the moving container is not properly pressurized when the moving container is in a non-inverted orientation.

* * * * *